United States Patent
Ebel et al.

(10) Patent No.: US 6,566,564 B1
(45) Date of Patent: May 20, 2003

(54) METHOD FOR ISOMERSING ALLYL ACOHOLS

(75) Inventors: Klaus Ebel, Lampertheim (DE); Frank Stock, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/130,827

(22) PCT Filed: Nov. 21, 2000

(86) PCT No.: PCT/EP00/11580

§ 371 (c)(1),
(2), (4) Date: May 23, 2002

(87) PCT Pub. No.: WO01/42177

PCT Pub. Date: Jun. 14, 2001

(30) Foreign Application Priority Data

Dec. 6, 1999 (DE) .......................................... 199 58 603

(51) Int. Cl.$^7$ .......................... C07C 35/00; C07C 27/00; C07C 29/00; C07C 27/20; C07C 27/22; C07C 27/24; C07C 29/15

(52) U.S. Cl. ...................... 568/875; 568/902; 568/909

(58) Field of Search ................................ 568/906, 875, 568/902, 873

(56) References Cited

FOREIGN PATENT DOCUMENTS

| DE | 25 16 698 | 10/1975 |
| GB | 1 256 184 | 12/1971 |

OTHER PUBLICATIONS

Chemistry Letters, pp. 357–360, 1982,Chem.Soc. of Japan, Hosogai et al.
Tetrahedron, vol. 33,pp. 1775–1783, Chabardes et al.

*Primary Examiner*—Samuel Barts
*Assistant Examiner*—Elvis O. Price
(74) *Attorney, Agent, or Firm*—Keil & Weinkauf

(57) ABSTRACT

Process for the isomerization of precursor allyl alcohols to product allyl alcohols in the presence of tungsten oxo(VI) complexes comprising additional nitrogen-containing ligands at temperatures of from 50 to 300° C., wherein, in the catalyst, as well as the nitrogen bases known as additional nitrogen-containing ligands, or instead of these nitrogen bases, aminoalcohols such as triethanolamine, diethanolamine, monoethanolamine, tripropanolamine, dipropanolamine, 3-amino-1-propanol, 1-amino-2-propanol, 2-amino-1-propanol, butyldiethanolamine, methyldiisopropanolamine, N,N'-bis(2-hydroxybenzyl)-1,2-diaminoethane or N-(2-hydroxybenzyl)amine are present as additional nitrogen-containing ligands. The process is particularly suitable for the preparation of tertiary product allyl alcohols, such as linalool, by isomerizing primary or secondary allyl alcohols, such as geraniol and nerol.

11 Claims, No Drawings

METHOD FOR ISOMERSING ALLYL ACOHOLS

This application is a 371 of PCT/EP00/11580, filed Nov. 21, 2000.

The present invention relates to an improved process for the isomerization of precursor allyl alcohols to product allyl alcohols in both directions of the equilibrium in the presence of tungsten oxo(VI) complexes comprising additional nitrogen-containing ligands.

Allyl alcohols are important intermediates in industrial organic chemistry. Tertiary allyl alcohols in particular are used, for example, as intermediates in the preparation of fragrances and also as additives in soaps or detergents.

It is known that allyl alcohols isomerize under acidic catalysis. This isomerization corresponds to a 1,3-migration of the hydroxyl group and a corresponding shift of the double bond, as shown in the equation below with the formulae I and II:

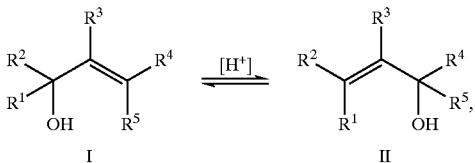

in which $R^1$ to $R^5$ are hydrogen or hydrocarbon radicals.

The process is particularly suitable for the preparation of tertiary product allyl alcohols, such as 2-linalool, by isomerization of primary or secondary allyl alcohols, such as geraniol and nerol.

Geraniol (2-trans-3,7-dimethyl-2,6-octadien-8-ol), nerol (2-cis-3,7-dimethyl-2,6-octadien-8-ol) and 2-linalool (3,7-dimethyl-1,6-octadien-3-ol) are important compounds in the fragrance industry. They are used either directly as fragrances, or are converted into higher molecular weight fragrances by reaction with other compounds. These terpene alcohols are also important as $C_{10}$ building blocks in the synthesis of vitamins, such as vitamin E.

In the past, preference has been given in the literature to the description of processes for the isomerization of linalool to geraniol. Since the isomerizations are equilibrium reactions, the processes developed can, in principle, also be used for the reverse reaction of the isomerization of geraniol or nerol to linalool.

Initially, the isomerization reactions of allyl alcohols were carried out using acids as catalysts. However, these processes were of only limited importance since during them secondary reactions, such as, for example, dehydrations or cyclizations, predominate.

Later, the catalytic rearrangement of substituted allyl alcohols using molybdenum, vanadium and tungsten catalysts was investigated (cf. P. Chabardes et al in Tetrahedron 33 (1977), pages 1775–1783.).

Whereas the molybdenum compound described in GB 1 256 184 as isomerization catalyst produced unsatisfactory reaction results, using tungsten oxo(VI) alkoxide catalysts of the formula $WO(OR)_4$ in the presence of a nitrogen base as additional ligand, relatively high selectivities coupled with simultaneously higher activities, compared with the analogous vanadium oxo(V) alkoxide catalysts of the formula $VO(OR)_3$, were possible. Further advantages of the tungsten catalysts are that they can be readily separated off from the reaction mixture (cf. T. Hosogai et al. in Chemistry Letters 1982, pages 357–360) and that they have only low toxicity compared with the vanadium catalyst.

Furthermore, DE 25 16 698 discloses the preparation of novel catalysts based on tungsten, and to the use thereof for the catalytic rearrangement of tertiary to primary allyl alcohols. In this process, the catalysts described are tungsten oxo(VI) complexes comprising alkoxy radicals and/or trialkylsilyl radicals bonded via oxygen, which, to improve the selectivity, additionally comprise ligands bonded coordinately to the tungsten, which comprise an element chosen from the elements N, P, As and Bi, in particular ligands chosen from the class of primary, secondary and tertiary monoamines, of polyamines, of Schiff's bases, of imines, nitriles and isonitriles. Ligands which are cited therein as particularly suitable are primary monoamines, such as methylamine, ethylamine, propylamine, β-ethoxyethylamine, butylamine, cyclohexylamine, alinine and naphthylamine; secondary monoamines, such as dimethylamine, diethylamine, dibutylamine, dicyclohexylamine, methylaniline, methylcyclohexylamine, piperidine, morpholine and pyrrolidine; tertiary monoamines, such as trimethylamine, triethylamine, ethyldibutylamine, tricyclohexylamine, dimethylaniline, pyridine, picoline, quinoline, isoquinoline, N-methylpyrrolidine and N-methylmorpholine; ethylenediamine, pyrazine, piperazine, pyrimidine, triethylenediamine, 1,8-diazabicyclo[5.4.0]undec-7-ene, polyethyleneimines, and ion exchanger resins having a large number of amino groups within the molecule, in particular pyridine, triethylamine, cyclohexylamine, diethylamine and tricyclohexylphosphine. Aminoalcohols are not mentioned therein. The selectivities for primary alcohols, such as nerol and geraniol, achieved with this process are extremely good, although the conversions achieved are still not ideal.

Our own investigations into the isomerization of geraniol using a 0.05 mol % strength solution of tungsten oxo(VI) tetrakis geranylate analogously to the process described in DE 25 16 698 have shown that the rearrangement to linalool proceeds in a significantly more selective manner in the presence of a nitrogen base at 200° C. (reaction time about 1 hour) than without co-use of a nitrogen base (see Comparatives Examples 1 to 5).

The nitrogen bases used here were diethylamine, pyridine, imidazole and poly(4-vinylpyridine).

Disadvantages of these experiments were the comparatively low conversions coupled with simultaneously high temperatures of more than 150° C., which accelerated the formation of by-products.

It is an object of the present invention to improve the process for the isomerization of allyl alcohols in the presence of tungsten oxo(VI) complexes comprising additional nitrogen-containing ligands at temperatures of from 50 to 300° C. such that, even in the case of the isomerization of primary or secondary allyl alcohols, such as geraniol and nerol, to tertiary allyl alcohols, such as linalool, relatively high conversions of the precursor allyl alcohol used are achieved, as a result of which the rate of the establishment of an equilibrium is accelerated, and the space-time yields increase.

Surprisingly, we have found that the process for the isomerization of precursor allyl alcohols to product allyl alcohols in the presence of homogeneously dissolved tungsten oxo(VI) complexes comprising additional nitrogen-containing ligands gives, coupled with selectivities which remain the same, higher activities for the isomerization of geraniol and nerol to linalool than corresponding isomerizations using tungsten oxo(VI) alkoxide catalysts in the presence of the known nitrogen bases alone if aminoalcohols are used as additional nitrogen-containing ligands.

A higher activity during the allyl rearrangement also results when the amino alcohols are added only subsequently to tungsten oxo(VI) alkoxide catalysts of the formula $WO(OR)_4$, to which nitrogen bases have already been added as additional ligands.

Accordingly, the invention provides a process for the isomerization of precursor allyl alcohols to product allyl alcohols in the presence of either preprepared or in-situgenerated tungsten oxo(VI) complexes comprising additional nitrogen-containing ligands at temperatures of from 50 to 300° C., wherein, in the catalyst, as well as the nitrogen bases known as additional nitrogen-containing ligands, or instead of these nitrogen bases, aminoalcohols are present as additional nitrogen-containing ligands.

Examples of allyl alcohols which can be advantageously isomerized using the process according to the invention and which may be mentioned are:

2-Methyl-3-buten-2-ol, prenol (3-methyl-2-buten-1-ol), linalool, nerol and geraniol, and farnesol (3,7,11-trimethyldodeca-2,6,10-trien-1-ol) and nerolidol (3,7,11-trimethyldodeca-1,6,10-trien-3-ol), in particular linalool, nerol and geraniol.

The aminoalcohols which can be used in the process according to the invention are aminoalcohols of the formula III,

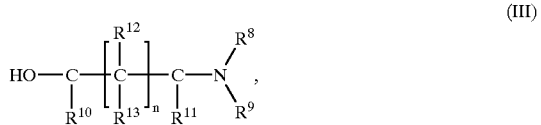

in which $R^8$ and $R^9$ are identical or different and are hydrogen, $C_1$- to $C_4$-alkyl, —$CH_2$—$C_6H_5OH$; —$C_2H_5OH$ or —$C_3H_7OH$, $R^{10}$ and $R^{11}$ are identical or different and are H, $C_1$- to $C_4$-alkyl, or together form a saturated or unsaturated divalent radical optionally substituted by $C_1$- to $C_4$-alkyl groups, $R^{12}$ and $R^{13}$ are identical or different and are hydrogen or a $C_1$- to $C_4$-alkyl radical, and n is an integer from 0 to 5.

The process according to the invention proceeds particularly advantageously if the aminoalcohols used are triethanolamine, diethanolamine, monoethanolamine, tripropanolamine, dipropanolamine, 3-amino-1-propanol, 1-amino-2-propanol, 2-amino-1-propanol, butyldiethanolamine, methyldiisopropanolamine, N-(2-hydroxybenzyl)amine or N,N'-bis(2-hydroxybenzyl)-1,2-diaminoethane.

For the preparation of the isomerization catalysts required for the process according to the invention, the tungsten oxo(VI) complexes used are generally the tungsten oxo(VI) complexes or tungsten oxo(VI) compounds described in DE 25 16 698 of the formulae

[WO(OR$^1$)(OR$^2$)(OR$^3$)(OR$^4$)]$_n$L

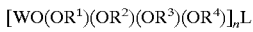

or

WO(OR$^1$)(OR$^2$)(OR$^3$)(OR$^4$),

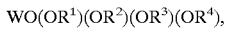

in which $R^1$ to $R^4$ are hydrocarbon groups, substituted hydrocarbon groups or groups of the formula

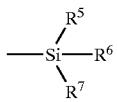

where $R^5$, $R^6$ and $R^7$ are each hydrocarbon groups which may optionally be substituted, where $R^1$, $R^2$, $R^3$ and $R^4$ may be identical or different and, if two or more of the groups $R^1$, $R^2$, $R^3$ and $R^4$ are hydrocarbons, irrespective of whether they are substituted or unsubstituted, two groups of this type can form a cyclic structure together with the adjacent tungsten and oxygen atoms in the formula, preferably compounds in which $R^1$, $R^2$, $R^3$, $R^4$, $R^5$, $R^6$ and $R^7$ are hydrocarbon groups chosen from the following groups: alkyl groups having 1 to 20 carbon atoms, alkenyl groups having 2 to 20 carbon atoms, cycloalkyl groups having 3 to 10 carbon atoms, cycloalkenyl groups having 3 to 10 carbon atoms, aryl groups having 6 to 10 carbon atoms, aralkyl groups having 7 to 20 carbon atoms, and alkylaryl groups having 7 to 20 carbon atoms, in particular compounds in which $R^1$ and $R^2$ are as defined above, $R^3$ and $R^4$ are hydrogen or a methyl group, or together form a saturated or unsaturated divalent radical, and $R^5$, $R^6$ and $R^7$ are hydrogen, L is a monovalent or polyvalent ligand which comprises nitrogen and is coordinately bonded to the tungsten atom in the formula via this nitrogen, and n is a value between 1 and the number of tungsten atoms which can be coordinately bonded to the ligand L.

The tungsten oxo(VI) complexes can be prepared, for example, in accordance with the processes described in DE 25 16 698 from tungsten trioxide with the hydroxyl compounds which contain groups corresponding to $R^1$, $R^2$, $R^3$ and $R^4$ in the presence of the ligand compound; or by reacting a tungsten oxytetrahalide with an alkali metal alkoxide of a hydroxyl compound containing groups corresponding to $R^1$, $R^2$, $R^3$ and $R^4$ in the presence of the ligand compound.

The tungsten oxo(VI) complex can, as described in DE 25 16 698, be prepared before the actual reaction, or else also be prepared directly in the reaction mixture.

For example, it is possible to add sodium tungstate dihydrate as solid to the precursor allyl alcohol, in this case geraniol. By heating the mixture to the temperature desired for the isomerization, the isomerization catalyst forms in the reaction mixture. The water eliminated during the catalyst formation is removed together with the isomerization product, in this case linalool, by reactive distillation.

The disclosure of DE 25 16 698 is therefore incorporated into this patent application by citation.

Generally, the tungsten oxo(VI) complexes are used dissolved in the precursor allyl alcohol in a concentration of from 0.001 to about 5% by weight.

The aminoalcohols are generally also advantageously used dissolved in the precursor allyl alcohol. They are generally used in an amount of from 1 mol % to 1000 mol %, preferably from 33 mol % to 500 mol %, based on the tungsten compound.

The set amount of the aminoalcohol ligand and, in particular, the amount of ligand compared with the amount of tungsten oxo(VI) complex used has an effect on the rate and the selectivity of the reaction.

A small amount of aminoalcohol ligand relative to the amount of tungsten effects a high rate of reaction, but also a somewhat lower selectivity, whereas a large amount of ligand produces the product with high selectivity but, under certain circumstances, a lower space-time yield.

The aminoalcohols are preferably used in an amount of from 100 mol % to 400 mol %, based on the total number of starting hydroxyl groups in the aminoalcohol and on the amount of tungsten, in particular in an amount of from 300 mol % to 400 mol %, based on the total number of starting hydroxyl groups in the aminoalcohol and on the amount of tungsten.

The absolute concentrations of ligand and tungsten complex in the reaction mixture are unimportant in the process according to the invention and can, for example, be increased such that the rate of the establishment of an equilibrium is increased in a desired manner.

An increase in the rate of the establishment of an equilibrium can also be achieved in the process according to the invention by removing water of reaction which has formed from the mixture, for example by passing over a stream of inert gas, adding known water-removing agents, or stripping with the stream of gas during the distillation.

In the tungsten oxo(VI) complexes, all or only some of the alcohol radicals on the tungsten atom which act as ligands, and all or only some of the nitrogen bases which act as additional ligands, can be replaced by the aminoalcohols added as additional ligands.

The process according to the invention is generally carried out at temperatures of from 50 to 300° C., preferably at from 150 to 250° C.

It can be carried out with and without co-use of a solvent, discontinuously, or else continuously.

Solvents which have proven particularly advantageous are, for example, the high-boiling secondary compounds of the allyl alcohol isomerization.

The process according to the invention can be advantageously carried out if the precursor allyl alcohols in the reaction mixture are present in a concentration of from about 10% by weight to 100% by weight.

The reaction mixture is worked up in a manner known per se.

A particularly advantageous process according to the invention is one where the precursor allyl alcohols used are geraniol and nerol, and the product allyl alcohol prepared is 2-linalool.

In this process, for work-up, 2-linalool is separated off from the product mixture as the lower-boiling component by distillation. In general, precursor allyl alcohols and secondary compounds will be present in the product allyl alcohol. The product allyl alcohol can be purified by distillation by known methods.

The isomerization is an equilibrium reaction and the position of the equilibrium depends on the thermodynamic properties of the precursor and product allyl alcohols, and on the reaction conditions. The discontinuous or continuous removal of linalool, the lowest-boiling allyl alcohol in the mixture, from the reaction batch permits, even in the case of an unfavorable establishment of an equilibrium as a result of the shift of the equilibrium, a favorable space-time yield, the reboiler of the distillation column serving as reaction chamber.

The examples and comparative examples below serve to illustrate the process according to the invention in more detail.

COMPARATIVE EXAMPLES 1* to 5*

The experiments for the isomerization of geraniol and nerol to 2-linalool were carried out in a 100 ml three-necked glass flask as reaction chamber fitted with internal thermometer, distillation bridge, gas supply pipe and a magnetic stirrer. The reaction flask was heated in a silicone oil bath for the reaction, and a continuous stream of 0.3 l/h of argon or nitrogen was passed over the stirred reaction solution. As soon as the precursor allyl alcohol had reached the required temperature, a calculated amount of the catalyst solution was added. The experiments were ended after 1 h by cooling, and the product composition was determined by means of gas chromatographic analysis (GC). During the reactions, no product was distilled off.

The catalyst solution was prepared by suspending 2 g (5.9 mmol) of $WOCl_4$ in 30 ml of toluene. After 10 g (63 mmol) of tetrahydrogeraniol had been added and a gentle stream of ammonia had been passed through, the mixture was filtered over 10 g of silica gel, and the silica gel was then washed with 5 ml of toluene. The combined filtrates gave the finished catalyst solution having a content of 0.13 M/l of tungsten.

After the reaction had been terminated by cooling, the product composition was determined by means of GEC. The low-boiling components given in Table 1 are dehydration products from geraniol, nerol and linalool. The high-boiling components given in Table 1 are compounds produced by ether formation from geraniol, nerol and linalool. The selectivity for linalool was determined from the quotient of the conversion to linalool and the overall conversion of geraniol. The geraniol used had a composition of 96% geraniol and about 4% nerol.

TABLE 1

| Comp. Examples | Nitrogen-containing base | Geraniol [GC area %] | 2-Linalool [GC area %] | Low-boiling components [GC area %] | High-boiling components [GC area %] |
|---|---|---|---|---|---|
| 1* | — | 50.7 | 17.7 | 5.4 | 18.1 |
| 2* | Diethylamine | 70.6 | 19.5 | 1.2 | 3.1 |
| 3* | Pyridine | 56.5 | 20.2 | 4.9 | 10.6 |
| 4* | Imidazole | 62.3 | 19.1 | 3.5 | 8.9 |
| 5* | Poly(4-vinyl-pyridine) | 72.8 | 17.1 | 1.4 | 3.6 |

Example 1 and Comparative Example 6* (as in DE 25 16 698)

Effect of an Aminoalcohol as Ligand

A mixture of in each case 20 g (0.13 mol) of geraniol, 1.0 ml (0.13 mmol) of the prepared tungsten oxo(VI) (tetrakisgeranylate) solution, and the nitrogen base diethylamine, shown in Table 2 below, and the aminoalcohol 1-amino-2-propanol in the molar ratio shown in Table 2 were heated at 200° C. for 1 h in a 100 ml three-necked glass flask. Subsequent GC of the reaction mixture gave the result shown in Table 2.

TABLE 2

| Examples and Comp. Examples* | Diethylamine:tungsten: 1-amino-2-propanol molar ratios | Geraniol [GC area %] | Linalool [GC area %] | Low-boiling components [GC area %] | High-boiling components [GC area %] | Selectivity to 2-linalool [%] |
|---|---|---|---|---|---|---|
| 6* | 2:1:0 | 66.0 | 26.1 | 0.9 | 3.4 | 87 |
| 1 | 2:1:3.5 | 47.7 | 42.2 | 1.2 | 3.0 | 87 |

The examples show that the reaction proceeds significantly more rapidly in the presence of 1-amino-2-propanol, coupled with constantly good selectivity, based on the 2-linalool formed.

EXAMPLES 2a to 2c

Effect of the Concentration of the Aminoalcohol Ligand

A mixture of in each case 20 g (0.13 mol) of geraniol, 1.0 ml (0.13 mmol) of the prepared tungsten oxo(VI) (tetrakisgeranylate) solution, and the aminoalcohol 1-amino-2-propanol in the molar ratio shown in Table 3 below were heated at 200° C. for 1 hour in a 100 ml three-necked glass flask. Subsequent GC of the reaction mixture gave the result shown in Table 3.

TABLE 3

| Examples | 2-Aminoethanol: tungsten molar ratio | Geraniol [GC area %] | Linalool [GC area %] | Low-boiling components [GC area %] | High-boiling components [GC area %] | Selectivity to 2-linalool [%] |
|---|---|---|---|---|---|---|
| 2a | 3:1 | 71.5 | 20.1 | 0.6 | 1.5 | 82 |
| 2b | 4:1 | 75.4 | 17.4 | 0.5 | 1.3 | 84 |
| 2c | 5:1 | 76.8 | 15.8 | 0.4 | 1.0 | 82 |

The examples show that the rate of the reaction decreases as the amount of 2-aminoethanol increases relative to the amount of tungsten, for a constant selectivity.

EXAMPLES 3a and 3b

Effect of Temperature

A mixture of in each case 90 g (0.59 mol) of geraniol, 1.5 ml (0.2 mmol) of the prepared tungsten oxo(VI) (tetrakisgeranylate) solution, and 1-amino-2-propanol, the nitrogen base diethylamine in the diethylamine:tungsten:1-amino-2-propanol molar ratio=2:1:3.5 were heated at the temperature shown in Table IV for 1 h in a 250 ml three-necked glass flask. Subsequent GC of the reaction mixture gave the result shown in Table 4.

TABLE 4

| Examples | Temperature (° C.) | Geraniol [GC area %] | Linalool [GC area %] | Low-boiling components [GC area %] | High-boiling components [GC area %] | Selectivity to 2-linalool [%] |
|---|---|---|---|---|---|---|
| 3a | 180 | 82.5 | 7.6 | 0.3 | 1.2 | 56 |
| 3b | 190 | 69.4 | 15.7 | 0.7 | 1.5 | 59 |

The examples show that at temperatures lower than 200° C., the use of 1-amino-2-propanol leads to a reduction both in the reactivity and in the selectivity of the catalyst.

EXAMPLES 4a and 4b

Effect of a Stream of Gas on the Reaction Rate

A mixture of in each 20 g (0.13 mol) of geraniol, 1.0 ml (0.13 mmol) of the prepared tungsten oxo(VI) (tetrakisgeranylate) solution, and the nitrogen base diethylamine and the aminoalcohol triethanolamine in the diethylamine:tungsten:triethanolamine molar ratio=2:1:1 were heated at 200° C. for 1 h in a 250 ml three-necked glass flask while passing over a continuous stream of argon. Subsequent GC of the reaction mixture gave the result shown in the Table V.

TABLE 5

| Examples | Gas stream | Geraniol [GC area %] | Linalool [GC area %] | Low-boiling components [GC area %] | High-boiling components [GC area %] | Selectivity to 2-linalool [%] |
|---|---|---|---|---|---|---|
| 4a | — | 76.4 | 16.3 | 0.3 | 1.0 | 83 |
| 4b | argon | 40.9 | 45.6 | 1.6 | 5.0 | 83 |

The examples show that water of reaction which is present in the reaction mixture has an inhibiting effect on the isomerization. By removing water using a stream of gas, the isomerization is accelerated.

We claim:

1. A process for the isomerization of precursor allyl alcohols to product allyl alcohols in the presence of preprepared or in-situ-generated tungsten oxo(VI) complexes comprising additional nitrogen-containing ligands at temperatures of from 50 to 300° C., wherein, in the catalyst, as well as the nitrogen bases known as additional nitrogen-containing ligands, or instead of these nitrogen bases, aminoalcohols are present as additional nitrogen-containing ligands.

2. A process as claimed in claim 1, wherein the aminoalcohols used are triethanolamine, diethanolamine, monoethanolamine, tripropanolamine, dipropanolamine, 3-amino-1-propanol, 1-amino-2-propanol, 2-amino-1-propanol, butyldiethanolamine, methyldiisopropanolamine, N-(2-hydroxybenzyl) amine or N,N'-bis(2-hydroxybenzyl)-1,2-diaminoethane.

3. A process as claimed in claim 1, wherein the tungsten oxo(VI) complex is dissolved in the precursor allyl alcohol in a concentration of from 0.001 to about 5% by weight.

4. A process as claimed in claim 1, wherein the aminoalcohol is dissolved in the precursor allyl alcohol in a concentration of from 1 mol % to 1000 mol %, based on the tungsten compound.

5. A process as claimed in claim 1, wherein the aminoalcohol is used dissolved in the precursor allyl alcohol in a concentration of from 33 mol % to 500 mol %, based on the tungsten compound.

6. A process as claimed in claim 1, wherein, in the tungsten oxo(VI) complexes, all or only some of the tungsten alkoxide ligands are replaced by the aminoalcohols added as additional ligands.

7. A process as claimed in claim 1, wherein primary or secondary precursor allyl alcohols are isomerized to tertiary product allyl alcohols.

8. A process as claimed in claim 1, wherein the isomerization is carried out at temperatures of from 150 to 250° C.

9. A process as claimed in claim 1, wherein the precursor allyl alcohols in the reaction mixture are present in a concentration of from 10% by weight to 100% by weight.

10. A process as claimed in claim 1, wherein the solvents used are the high-boiling secondary compounds of the allyl alcohol isomerization.

11. A process as claimed in claim 1, wherein the precursor allyl alcohols used are geraniol and nerol, and the product allyl alcohol prepared is 2-linalool.

* * * * *

UNITED STATES PATENT AND TRADEMARK OFFICE
CERTIFICATE OF CORRECTION

PATENT NO. : 6,566,564 B1  Page 1 of 1
DATED : May 20, 2003
INVENTOR(S) : Ebel et al.

It is certified that error appears in the above-identified patent and that said Letters Patent is hereby corrected as shown below:

<u>Title page, Item [54] and Column 1, lines 1 and 2,</u>
"ACOHOLS" should be -- ALCOHOLS --.

<u>Column 10,</u>
Line 4, delete "used".

Signed and Sealed this

Eighth Day of July, 2003

JAMES E. ROGAN
*Director of the United States Patent and Trademark Office*